US00PP13904P29

(12) United States Plant Patent
Kobayashi

(10) Patent No.: US PP13,904 P2
(45) Date of Patent: Jun. 24, 2003

(54) POINSETTIA PLANT NAMED 'WINROSE'

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/087,972

(22) Filed: Mar. 4, 2002

(51) Int. Cl.[7] ..... A01H 5/00
(52) U.S. Cl. ..... Plt./307

(58) Field of Search ..... Plt./307, 303

*Primary Examiner*—Bruce R. Campell
*Assistant Examiner*—June Hwu
(74) *Attorney, Agent, or Firm*—C. A. Whealy

(57) ABSTRACT

A new and distinct cultivar of Poinsettia plant named 'Winrose', characterized by its ball-shaped inflorescences with recurved red-colored flower bracts; recurved dark green-colored leaves; uniform plant habit; very early flowering; and excellent postproduction longevity.

1 Drawing Sheet

BOTANICAL CLASSIFICATION/CULTIVAR DESIGNATION

*Euphorbia pulcherrima* Willd. cultivar Winrose.

BACKGROUND OF THE INVENTION

The present Invention relates to a new and distinct cultivar of Poinsettia plant, botanically known as *Euphorbia pulcherrima* Willd., and hereinafter referred to by the name 'Winrose'.

The new Poinsettia a product of a induced mutation breeding program conducted by the Inventor in Encinitas, Calif. The objective of the breeding program is to create new Poinsettia cultivars having strong stems, reflexed flower bracts with desirable colors, uniform plant habit and excellent post-production longevity.

The new Poinsettia is an induced mutation of the *Euphorbia pulcherrima* Willd. cultivar Windark, disclosed in U.S. Plant Pat. No 12,546. Mutations were induced by exposing unrooted cuttings of 'Windark' to gamma radiation. The new Poinsettia was discovered and selected by the Inventor as a single flowering plant within a population of irradiated plants of the cultivar Windark on Aug. 23, 1999, in a controlled environment in Encinitas, Calif. The selection of this plant was based on its strong stems and reflexed red-colored flower bracts.

Asexual reproduction of the new Poinsettia by terminal cuttings propagated in a controlled environment in Encinitas, Calif., since late August, 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Winrose'. These characteristics in combination distinguish 'Winrose' as a new and distinct cultivar:

1. Ball-shaped inflorescences with recurved red-colored flower bracts.
2. Recurved dark green-colored leaves.
3. Uniform plant habit.
4. Strong erect stems.

5. Very early flowering; natural season flower maturity date is mid-November for plants grown in Encinitas, Calif.; response time, about 7 weeks.
6. Excellent post-production longevity.

Plants of the new Poinsettia are most similar to the parent, the cultivar Windark. Plants of the new Poinsettia differ primarily from plants of the parent in flower bract coloration as plants of the cultivar Windark have dark red-colored flower bracts.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a side perspective view of a typical flowering plant of 'Winrose' grown in a 16.5-cm container.

The photograph at bottom of the sheet is a close-up view of typical leaves and flower bracts of 'Winrose'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polycarbonate-covered greenhouse with day temperatures about 24 to 29° C., night temperatures about 19° C., and light levels about 4,000 foot-candles. Single plants were grown in 16.5-cm pots and pinched once. Plants were flowered under natural season short day/long night conditions. Plants were about 16 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Winrose.

Parentage: Induced mutation of *Euphorbia pulcherrima* Willd. cultivar Windark, disclosed in U.S. Plant Pat. No. 12,546.

Propagation:

*Type cutting.*—Terminal cuttings.

*Time to initiate roots.*—About 10 days at 20 to 22° C.

*Time to develop roots.*—About 28 days at 24° C.

*Root description.*—Thick, fibrous and freely-branching.

Plant description:

*Plant form.*—Inverted triangle; strong and erect stems.

*Growth habit.*—Upright and uniform plant habit. Moderately vigorous.

*Plant height.*—About 23.5 cm.

*Plant diameter or spread.*—About 26 cm.

*Lateral branch description.*—Quantity: About three to four lateral branches develop after pinching. Length: About 19 cm. Diameter: About 6 mm. Internode length: About 1.75 cm. Strength: Strong, stiff. Texture: Smooth; glabrous. Color: 146B.

*Foliage description.*—Arrangement: Alternate, single. Quantity of leaves per lateral branch: About eight. Length: About 10 cm. Width: About 8.5 cm. Shape: Roughly ovate. Apex: Acuminate. Base: Obtuse to truncate. Margin: Entire; somewhat sinuate. Venation pattern: Pinnate. Texture: Upper surface: Glabrous. Lower surface: Slightly pubescent. Surface: Rugose. Orientation: Recurved. Color: Young and fully expanded foliage, upper surface: Darker than 147A. Young and fully expanded foliage, lower surface: 137B. Venation, upper surface: 144C. Venation, lower surface: 145B. Petiole: Length: About 2 cm. Diameter: About 4 mm. Texture, upper and lower surfaces: Smooth; glabrous. Color: 185A.

Inflorescence description:

*Inflorescence type and habit.*—Inflorescences are compound corymbs of cyathia with colored flower bracts subtending the cyathia. One inflorescence per lateral branch. Flower bracts recurved, inflorescences ball-shaped. Flowers are not fragrant. Flowers persistent.

*Natural flowering season.*—Autumn/winter in Northern Hemisphere. Flower initiation and development is induced under long nyctoperiod conditions. Very early flowering, response time, about 7 weeks; natural season flower maturity date is mid-November for plants grown in Encinitas, Calif.

*Post-production longevity.*—Plants of the new Poinsettia maintain good substance and bract color for about four weeks under interior conditions.

*Inflorescence size.*—Diameter: About 12 cm. Height (depth): About 5 cm.

*Flower bracts.*—Quantity per inflorescence: About 24. Length, largest bracts: About 6.5 cm. Width, largest bracts: About 6 cm. Shape: Ovate to elliptic. Apex: Acuminate, curled. Base: Obtuse. Margin: Entire; somewhat sinuate. Texture, upper and lower surfaces: Glabrous; velvety. Surface: Rugose. Orientation: Recurved. Venation pattern: Pinnate. Color: Developing or transitional bracts, upper surface: 45B. Developing or transitional bracts, lower surface: 45C. Fully developed bracts, upper surface: 45B to 45C; color fading to 45C to 47A with subsequent development. Fully developed bracts, lower surface: 45D. Venation, upper and lower surfaces: Similar to flower bract color. Bract petiole: Length: About 1.3 cm. Diameter: About 2.5 mm. Texture, upper and lower surfaces: Smooth; glabrous. Color: 60A.

*Cyathia.*—Quantity: About 10 per corymb. Diameter of cyathia cluster: About 2 by 2.5 cm. Length: About 1 cm. Width: About 5 mm. Shape: Ovoid. Color: Immature: 145A. Mature: 144A. Peduncle: Length: About 2 mm. Diameter: About 2 mm. Strength: Strong. Aspect: Mostly upright. Texture: Smooth; glabrous. Color: 145B. Stamens: Quantity per cyathium: At least 10. Anther shape: Oval. Anther length: Less than 1 mm. Anther color: 45C. Amount of pollen: Scarce. Pollen color: 12A. Pistils: None observed. Nectaries: Quantity per cyathium: One. Size: About 3 mm by 3 mm. Color: 13A.

Disease/pest resistance: Resistance to pathogens and pests common to Poinsettias has not been observed on plants grown under commercial conditions.

It is claimed:

1. A new and distinct cultivar of Poinsettia plant named 'Winrose', as illustrated and described.

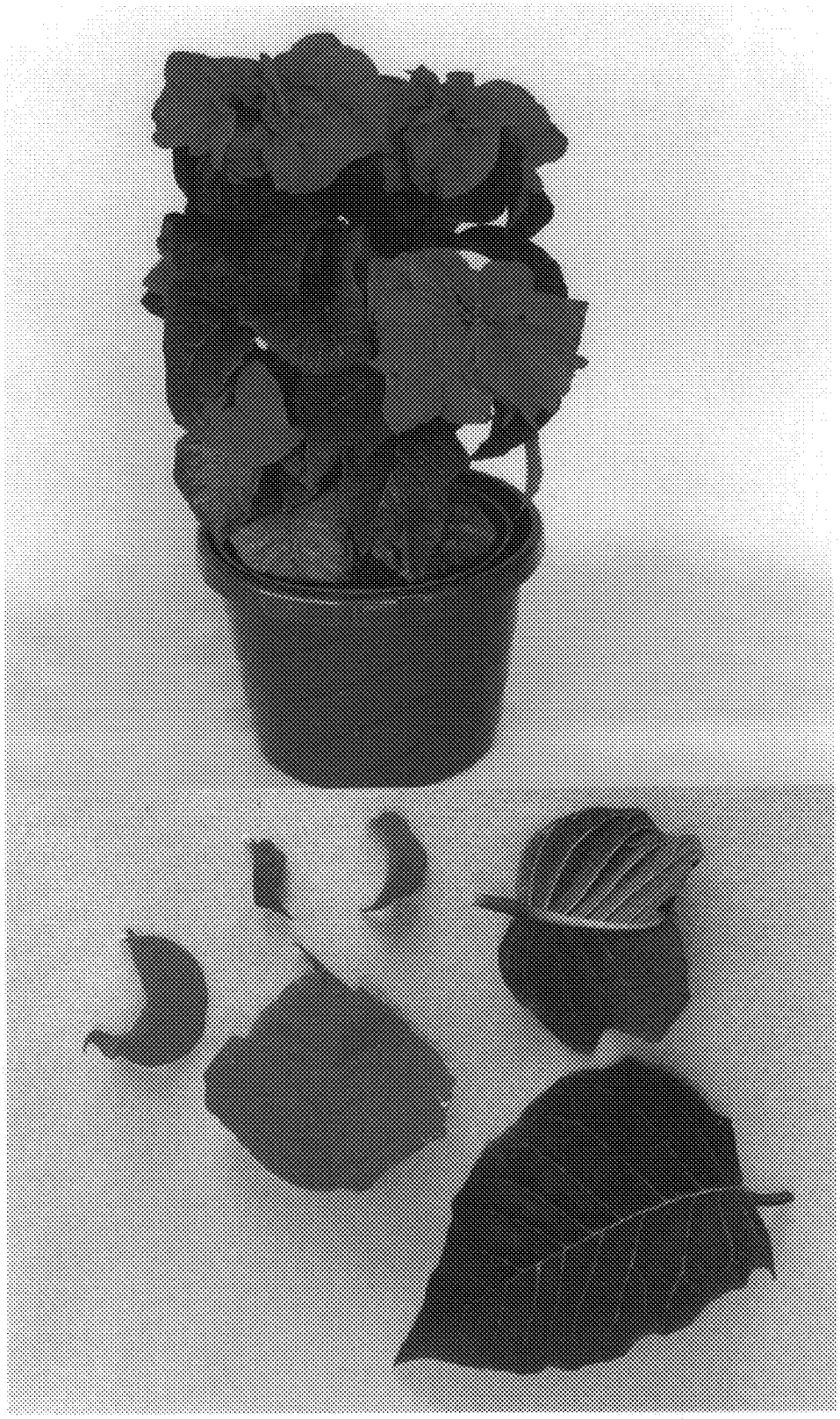

* * * * *